United States Patent
Edwards

(10) Patent No.: US 7,372,263 B2
(45) Date of Patent: May 13, 2008

(54) APPARATUS AND METHOD FOR MEASURING CASED HOLE FLUID FLOW WITH NMR

(75) Inventor: Carl Edwards, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 41 days.

(21) Appl. No.: 11/286,627

(22) Filed: Nov. 23, 2005

(65) Prior Publication Data

US 2007/0114996 A1  May 24, 2007

(51) Int. Cl.
*G01V 3/00* (2006.01)
(52) U.S. Cl. .................................. 324/303
(58) Field of Classification Search ......... 324/300–322
See application file for complete search history.

(56) References Cited

U.S. PATENT DOCUMENTS

| | | | |
|---|---|---|---|
| 4,745,802 A | 5/1988 | Purfurst | |
| 4,785,245 A | 11/1988 | Lew et al. | |
| 4,901,018 A | 2/1990 | Lew | |
| 5,122,746 A | 6/1992 | King et al. | |
| 5,216,366 A | 6/1993 | Young | |
| 5,247,830 A | 9/1993 | Goode | |
| 5,289,124 A * | 2/1994 | Jerosch-Herold et al. | ... 324/303 |
| 5,291,138 A | 3/1994 | Macovski | |
| 5,387,865 A * | 2/1995 | Jerosch-Herold et al. | ... 324/303 |
| 5,532,593 A | 7/1996 | Maneval et al. | |
| 5,539,309 A | 7/1996 | Van Wyk et al. | |
| 5,684,399 A | 11/1997 | Bayer | |
| 5,949,060 A | 9/1999 | Schattschneider et al. | |
| 5,949,069 A | 9/1999 | Chace et al. | |
| 6,046,587 A | 4/2000 | King et al. | |
| 6,047,239 A | 4/2000 | Berger et al. | |
| 6,268,727 B1 | 7/2001 | King et al. | |
| 6,601,461 B2 | 8/2003 | Maxit et al. | |
| 6,642,715 B2 | 11/2003 | Speier et al. | |
| 6,720,765 B2 | 4/2004 | Edwards et al. | |
| 6,755,086 B2 | 6/2004 | Salamitou et al. | |
| 6,755,247 B2 | 6/2004 | Moake et al. | |
| 6,841,996 B2 * | 1/2005 | Madio et al. | ............... 324/303 |
| 6,856,132 B2 * | 2/2005 | Appel et al. | ................ 324/303 |
| 6,952,096 B2 * | 10/2005 | Freedman | .................... 324/303 |
| 7,180,288 B2 * | 2/2007 | Scheven | ..................... 324/303 |

OTHER PUBLICATIONS

Karczmar, Twieg, Lawry, Matson, & Weiner, Detection of Motion Using B1 Gradients, Magnetic Resonance in Medicine 7, 111-116 (1988).

(Continued)

*Primary Examiner*—Brij Shrivastav
*Assistant Examiner*—Dixomara Vargas
(74) *Attorney, Agent, or Firm*—Bracewell & Giuliani LLP

(57) ABSTRACT

A method and apparatus useful to determine characteristics of fluid flow, such as fluid holdup and flow velocity. The apparatus comprises a flow tube, a permanent magnet, a first set of coils, and a second set of coils. The first set of coils creates a radio frequency magnetic field within the flow tube with a series of refocusing pulses. The second set of coils encodes velocity information onto the fluid molecules using rotating frame zeugmatography that is later decoded and used to estimate the fluid flow velocity.

14 Claims, 16 Drawing Sheets

OTHER PUBLICATIONS

Metz, Boehmer, Bowers, & Moore, Rapid Rotating-Frame Imaging Using an RF Pulse Train (RIPT), Journal of Magnetic Resonance, Series B103, 152-161 (1994).

Maffei, Mutzenhardt, Retournard, Diter, Raulet, Brondeau, & Canet, NMR Microscopy by Radiofrequency Field Gradients, Journal of Magnetic Resonance, Series A 107, 40-49 (1994).

Humbert, Diter, & Canet, NMR Microscopy by Strong Radiofrequency-Field Gradients with Spatial Resolution Better Than Five Micrometers, Journal of Magnetic Resonance, Series A 123, 242-245 (1996).

D. I. Hoult, NMR Imaging, Rotating Frame Selective Pulses, Journal of Magnetic Resonance 38, 369-374 (1980).

D. I. Hoult, Rotating Frame Zeugmatography, Journal of Magnetic Resonance 33, 183-197 (1979).

Eiichi Fukushima, Nuclear Magnetic Resonance as a Tool to Study Flow, Annu. Rev. Fluid Mech. 1999, 31:95-123.

F. De Luca, Full-Rotating Frame NMR Imaging, Lettere Al Nuovo Cimento, vol. 39, N. 16, Apr. 21, 1984.

Davydov and Semenov, A Modulation Operating Mode for Nutation NMR Flowmeters and Magnetometers, Instruments & Experimental Techniques, vol. 42, No. 1, 1999, pp. 427-429.

D. Canet, Les Gradients de Champ Radio-frequence (gradients B1) en RMN, J. Chlm Phys (1995) 92, 1893-1904.

Bougeois and Decorps, A B1-Gradient Method for the Detection of Slow Coherent Motion, Journal of Magnetic Resonance 91, 128-135 (1991).

\* cited by examiner

APPARATUS AND METHOD FOR MEASURING CASED HOLE FLUID FLOW WITH NMR

BACKGROUND OF THE INVENTION

1. Field of the Invention

The present invention relates to a method and apparatus for estimating fluid flow. More specifically the present invention relates to methods and apparatus for evaluating fluid flow within a borehole.

2. Description of Related Art

The sampling of hydrocarbon producing wellbores, such as by well logging, can yield a litany of information useful in assessing the potential location and reserves of a given wellbore. The information may include permeability, porosity, bound fluid volume, formation pressure and temperature, and resistivity. Estimates of one or more of these borehole parameters in a specific formation can be made by sending signals from logging instruments inserted downhole. These parameters can also be determined by mechanically extracting fluids from within the formation. This can be done by a drill stem test or with an instrument that extracts fluids from the formations.

One example of a device that mechanically extracts fluid from within the formation is a formation test tool. Once inside of a borehole, a probe from the device is inserted past the mud cake to come in contact with the formation itself. Fluid is then withdrawn from the formation into the tool for subsequent sampling. After the sampling sequence, the formation pressure can be measured as it builds back up to its natural formation pressure. Models exist for estimating permeability based on the formation pressure and temperature tool data. These models may include a laminar or spherical model design. Examples of such devices can be found in the following references: U.S. Pat. No. 6,047,239, U.S. Pat. No. 5,2447,830, U.S. Pat. No. 5,949,060, and U.S. Pat. No. 4,745,802. Some drawbacks exist however with these formation test tools. Each sampling sequence requires that the sample point be at formation pressure. Since each sampling event necessarily reduces the pressure at the sample point, it may require from several minutes up to in excess of an hour to conduct subsequent sampling events.

Nuclear magnetic resonance (NMR) devices have also been utilized in estimating the formation permeability and/or fluid flow of the formation fluid. Generally, devices using NMR in well logging include a permanent magnet that generates a static magnetic field within the region of the formation to be investigated. Atomic nuclei contain magnetic moments associated with their nuclear spin. In the absence of an applied magnetic field, thermal fluctuations cause these moments to have random orientations in space. When these nuclei are subjected to a static magnetic field, the magnetic moments tend to align either parallel or antiparallel to this applied field. The permanent magnet associated with the NMR devices orients the magnetic moments of the nuclei in the area being assessed. NMR devices also usually include a transmitter coil for inducing a radio frequency (RF) magnetic flux. The transmitter coil is typically oriented such that the magnetic field produced by the coil is substantially perpendicular to that of the static magnetic field. Also, a receiver coil for receiving reflected signals is included with the NMR tool.

In operation, the transmitter coil induces a RF magnetic pulse that reorients the magnetic moments of the nuclei along a direction that is perpendicular to both the direction of the static field of the permanent magnet and to the direction of the applied RF pulse. The pulse is maintained until the spin moments are perpendicular to the static field. Then the spins realign with the static magnetic field in a time period referred to as the spin-lattice relaxation rate $T_1$. Moreover, the magnetic moments of the nuclei are out of alignment with the field produced by the permanent magnet. As such a perpendicular force is applied such that they precess around the region of the static field. The rate at which they precess is referred to as the Larmor frequency.

Theoretically, while precessing the spin vectors are generally aligned, however because the static field is inhomogeneous, the spins may precess at different rates. This in turn decays the different precession rates of the vector sum of the magnetization in the plane of the spins to zero. The decay rate, $T_2^*$, is typically referred to the free induction decay (FID). Another magnetic pulse with twice the duration of the first pulse can then be applied that flips the spin vectors 180°. The leading and lagging spins now switch position. Due to this phenomenon, the magnetization vectors can reconverge. Ultimately the spin vectors are realigned. Realignment creates a spin echo that is recordable by the receiver coil. Increasing the time between the excitation pulse and the realignment pulse is increased in turn decays the spin echo amplitude. The characteristic decay time ($T_2$) is referred to as the spin-spin or transverse relaxation time. The amplitude of the spin echoes can be used to determine spin density, $T_1$ and $T_2$. The amplitudes of successive echoes decay with $T_2$. Upon obtaining the $T_2$ distributions, other formation characteristics, such as permeability, may be determined.

Typically $T_2$ distributions are measured using an error-correcting step, such as a Carr-Purcell-Meiboom-Gill (CPMG) NMR pulse sequence. In order to provide meaningful results, the length of the recorded echo train must be at least as the maximum $T_2$ of the spin system. During this time period, as well as during the preceding prepolarization period, the measurement is sensitive to displacements of the measuring device. Further, in some cases, the $T_2$ distributions do not represent pore size distributions. Hydrocarbons in water wet rocks can change the correlation between $T_2$ distribution and pore size distribution. Finally, the correlation between pore size distribution and permeability of the formation is achieved using several formulas based on large measured data sets, displaying relatively weak correlation. In carbonates, these formulae breakdown because of the formations' complex pore shapes.

Other types of flow meters are found in U.S. Pat. No. 6,755,086, and U.S. Pat. No. 6,601,461, and U.S. Pat. No. 4,901,018 (NMR), and U.S. Pat. No. 6,046,587. However, these NMR devices and methods developed heretofore, fail to provide an accurate means of evaluating fluid flow of formation fluid while downhole. Therefore, there exists the need for a method and device capable of being insertable into a borehole intersecting a hydrocarbon producing formation, and measuring fluid flow of fluid within the formation.

BRIEF SUMMARY OF THE INVENTION

The present disclosure includes a method of measuring fluid flow comprising, applying a static magnetic field to the flow and applying at least one electromagnetic pulse sequence to the flow. The electromagnetic pulse considered herein comprises a rotating frame portion and a refocusing portion, wherein the electromagnetic pulse sequence produces signals. The method further includes analyzing the signals to determine fluid flow. Optionally, the at least one electromagnetic pulse sequence comprises a CPMG sequence. Also, the refocusing pulses in the generalized CPMG may be spaced 180° from one another. Additionally, the signals can be echoes. The rotating frame portion of the electromagnetic pulse sequence can comprise encoding the position of fluid flow molecules then decoding the position of the fluid flow molecules at a later time.

The rotating frame portion of the electromagnetic pulse sequence may comprise, emitting a first magnetic pulse having a gradient in real space substantially aligned with a first axis and having a radio frequency field orientation in the rotating frame that is substantially orthogonal to the first axis, and emitting a second magnetic pulse having a gradient in real space substantially aligned with the first axis and having a radio frequency field orientation in the rotating frame that is substantially orthogonal to the first axis in a direction opposite to the radio frequency field of the first magnetic pulse.

The present method may further comprise determining fluid flow velocity from the residual nutation angle between the encoded fluid flow molecules and the decoded fluid flow molecules. Additionally, the refocusing portion of the electromagnetic pulse sequence may comprise a CPMG sequence. The CPMG sequence can take place within an x-y coordinate system and comprise a pulse having an orientation and pattern of 90y -TE/2-180x-TE-180x-TE-180x-TE. The present method can further comprise analyzing the signal echoes to determine fluid holdup. Optionally the fluid holdup can be determined by integrating the amplitudes of the signal echo in the T2 domain. Moreover, the fluid may be selected from the list consisting of single-phase fluid, two-phase fluid, and three-phase fluid. The present method may further comprise measuring fluid flow within a wellbore. Additionally, the method of measuring flow may further comprise analyzing the signals to determine characteristics of the fluid.

The present disclosure considers an alternative method of measuring fluid flow comprising, subjecting a portion of the fluid to a static magnetic field, encoding fluid velocity data by applying a first radio frequency magnetic field to the portion of the fluid using rotating frame zeugmatography, and evaluating the fluid velocity of the fluid flow using the encoded velocity data.

DETAILED DESCRIPTION OF THE INVENTION

Figure 1A:
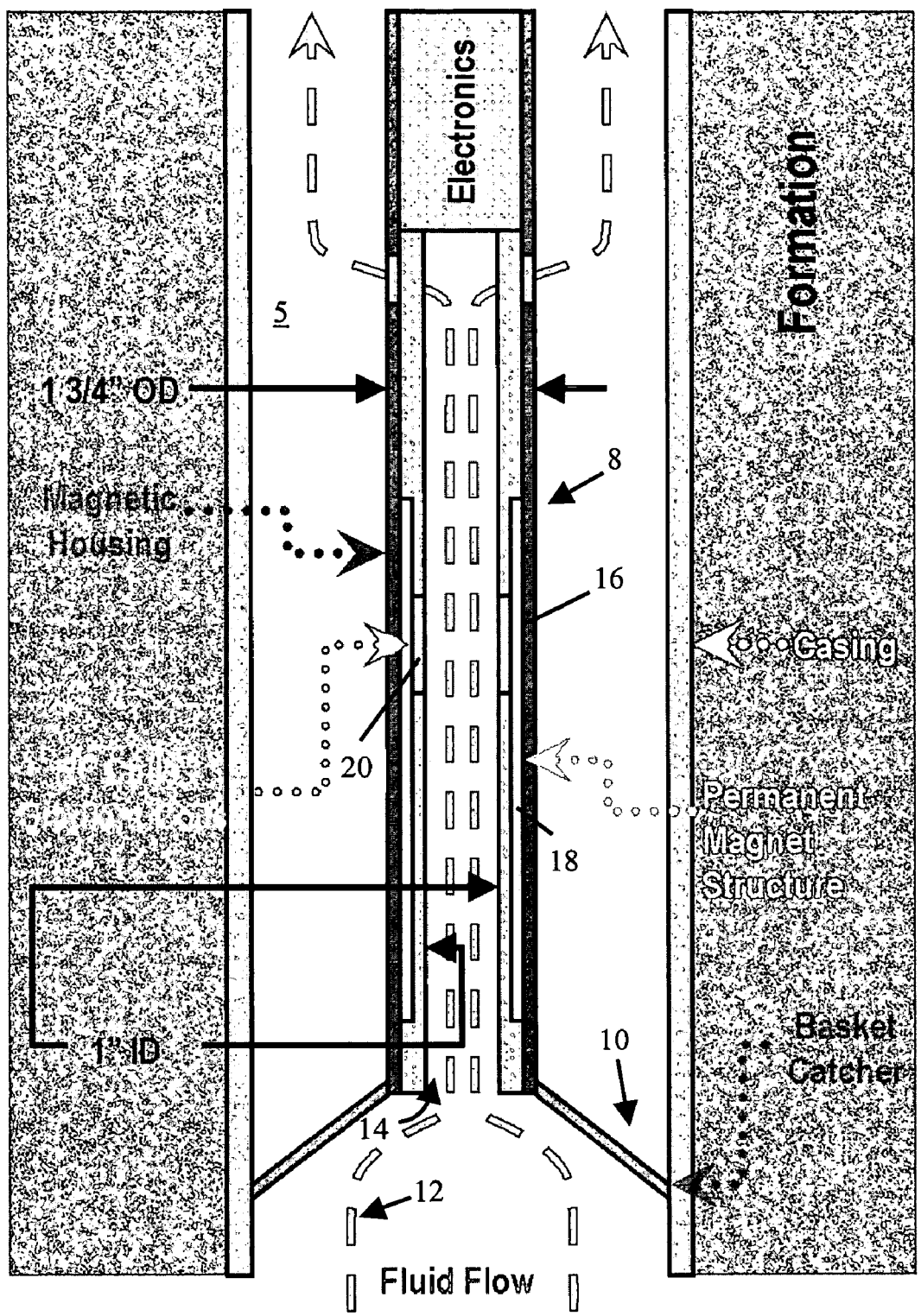
FIG. 1a depicts a cross-section of an embodiment of a portion of a flowmeter in accordance with the present disclosure.

A cross-section of an embodiment of a flow meter 8 in accordance with the present disclosure is shown in FIG. 1*a*. The flow meter 8 is shown coaxially disposed within a wellbore 5, fluid flow through the flow meter 8 is illustrated by the dashed lines 12. When it is disposed in the wellbore 5, the flowing fluid is diverted by into a channel 14 by a basket catcher 10, although those skilled in the art will understand that any means of diverting the flow may be used. For purposes of convenience, the direction of flow is labeled as the z-axis of this embodiment.

Surrounding the flow channel 14 is a generally annular housing 16 that contains the means for magnetizing the nuclei in a first volume of the fluid. The length of this first volume in the z-direction is constrained by the requirement that the fluid is fully polarized when it reaches a second volume known as the sensitive volume contained within the first volume. It is defined more fully below. In this embodiment the magnetizing means comprises a number of permanent magnets 18 oriented so that the static magnetic field, $B_0$, generated therefrom is substantially uniform and substantially oriented perpendicular to the z-axis in the sensitive volume. The direction of the static magnetic field is labeled the x-axis. Those skilled in the art will recognize that any method of generating a static magnetic field over the time period long compared to the measurement time and to the relaxation times of the nuclei in flowing fluids could be used. They will also recognize that $B_0$ need not be substantially uniform or oriented in any particular manner in the portion of the first volume that is outside the sensitive volume as long as the magnetized nuclei experience magnetic field that changes adiabatically as they flow through the first volume.

A second annular region houses the means for exciting the nuclei within the second volume of the fluid and detecting the NMR signal that emanates there from. In this embodiment, this means is a coil 20 that generates a first oscillating magnetic field, $B_1$, whose orientation is substantially perpendicular to both the static magnetic field and the flow direction. The second volume is defined by the condition that the both the static and oscillating magnetic fields are substantially uniform and the oscillating magnetic field is substantially perpendicular to the static magnetic field. The y-axis is defined as being perpendicular to the flow axis and the static magnetic field. The oscillating magnetic field of this means being oriented generally along this axis. The frequency of the oscillating magnetic field must approximately satisfy Larmor's equation.

$$f = \gamma B_0 / 2\pi,$$

where $\gamma$ is the gyromagnetic ratio of the excited nuclei and $B_0$ is the static magnetic field in the second volume. The time dependence of the oscillating magnetic field is controlled by the electronics and the NMR signals detected by this means are recorded by the electronic means as well. Those skilled in the art will understand that these conditions on the orientation and the uniformity of the oscillating magnetic field can be relaxed but the resulting embodiments of the invention may not be optimal.

Finally the second annular region houses a means for generating a second oscillating magnetic field, $g_z$, whose amplitude varies linearly over the second volume. The orientation of this oscillating magnetic is substantially oriented perpendicular to the static magnetic field, but can be unrelated to any other orientation previously described. Its time dependence is controlled by the electronic means. In the preferred embodiment the orientation of this oscillating magnetic field is also perpendicular to the first oscillating magnetic field. This minimizes the coupling between the means of generating the first oscillating magnetic field and the means for generating the second oscillating magnetic field but is not required. Also in the preferred embodiment, the direction of linear variation is along the direction of flow. Those skilled in the art will recognized that condition of linearity can be relaxed to include any function that varies monotonically in the second volume.

Thus in the preferred embodiment, a number of magnetic field are generated. In the second volume, these fields can be written as approximations as $$B_0 = B_0 x,$$

$$B_1(t) = B_1(t) \cos(2\pi f t + \phi_1) y,$$

$$g_z(t,z) = g_z(t) z \cos(2\pi f t + \phi_2) z.$$

The frequency, amplitude, and phase of the oscillating magnetic fields $B_1$ and $g_z$ are controlled by the electronic means.

Holdup and flow measurements are made on fluid within the sensitive volume. As fluid diverted from the borehole to the channel by the basket catcher passes into the sensitive volume (also referred to herein as an elongated fluid flow test region), NMR experiments are performed to estimate the fraction of borehole fluid that is oil or water and the velocity thereof. After the measurement is performed, the fluid passes out of the tool as shown in the figure. It should be pointed out that the apparatus and method described herein is not limited to estimating simply oil and water holdup, but can also be used to estimate fluid flow information, such as holdup and velocity, of fluids comprised of liquid and gas as well as three phase mixtures of two immiscible liquid phases and a gas phase.

The Means for Generating the Static Magnetic Field

Figure 1B:
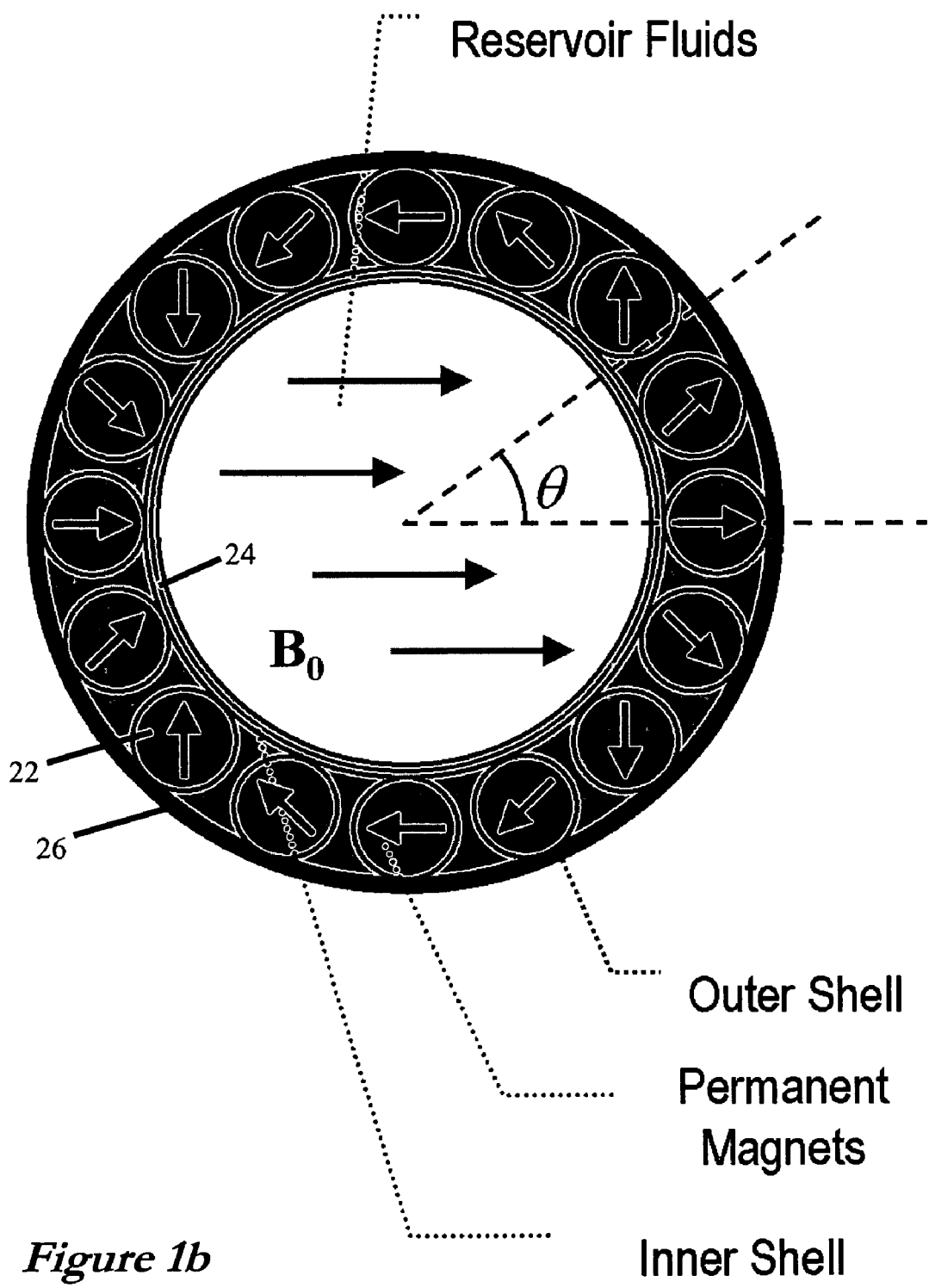
FIG. 1b depicts an axial cross-section of an embodiment of a portion of a flowmeter in accordance with the present disclosure.

A cross-section of one embodiment of a means for generating $B_0$ is shown in FIG. 1b. The structure consists of a number of uniformly magnetized rods 22 spaced about the circumference of a cylinder 24. Each rod 22 is magnetized substantially perpendicular to its cylindrical axis. The direction of the magnetization, $M_{rod}$, of each rod 22 varies with its placement within the structure to give a substantially uniform magnetic field within the interior of the structure. If the rod 22 is placed at an angle, $\theta$, with respect to an axis, then the direction of magnetization is then $2\theta$.

$$M_{rod}(\theta) = M_r(x \cos 2\theta + y \sin 2\theta), \quad (1)$$

where $M_r$ is the remnant magnetization of the magnet material. In FIG. 1b, the direction of the magnetic field $B_0$ is substantially along the x-axis in the interior of the structure.

Figure 2:
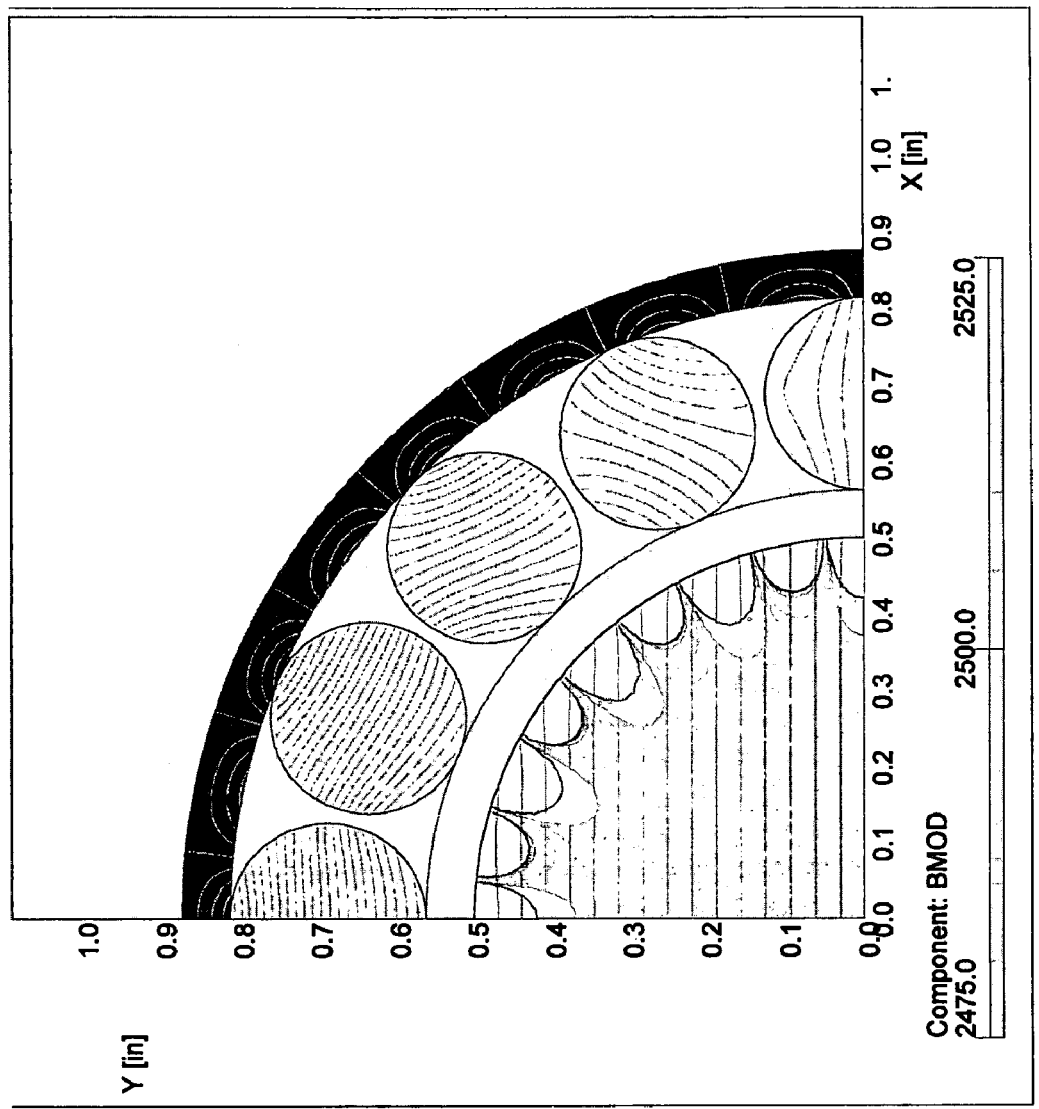
FIG. 2 portrays a contour plot of a static magnetic field of an embodiment of a flowmeter in accordance with the present disclosure.

FIG. 2 shows an example of a contour plot of the interior of the flow meter 8 with a 16 rod configuration. Only ¼ of the configuration is shown in FIG. 2 due to the symmetry of the configuration. The magnetic field, $B_0$, is approximately 2660±10 G in the central part of the flow meter to a radius of about 0.4 inches when the modeled magnetic material is $SaCo_5$. The field is oriented substantially along the x-axis of the diagram. The magnitude of the field is proportional to the magnetization of the rods as well as the total cross-section of the magnet material. So, the magnitude of the field can be changed by using materials with different magnetizations or by using rods of different sizes. The uniformity of the magnetic field depends on the number of rods used. The magnetic field generated by an eight-rod configuration is less homogeneous than a 16 rod configuration.

The configuration of the magnet of FIG. 2 is not limited to using a single layer of rods. Multiple layers of rods could be used to improve the homogeneity of the field in the interior of the flow meter. In addition, the shape of the magnetic material is also unimportant. Rods are used in this embodiment because magnetizing the rods and assembling them into the structures shown in FIGS. 1a, 1b, and 2 is simplified. However, any shape could be used as long as the magnetization satisfies eqn. (1).

The configurations shown in FIGS. 1a and 1b can be made any length and each rod could be segmented along the z-axis to improve manufacturability. The length of the magnet configuration is determined by the requirements of fluid prepolarization. That is, the need to polarize the hydrogen atoms in the fluid to a known condition prior to NMR excitation.

Also shown in FIG. 1 is an outer shell 26. Models reveal that the magnetic properties of this material are unimportant. Highly permeably materials could be used without substantially affecting the static field inside the flow meter. This is particularly appealing because this would lessen the effect of magnetic casing on the flow meter's magnetic field.

The Means for Generating the First Oscillating Magnetic Field

NMR requires at least one component of the oscillating magnetic field be substantially perpendicular to the static magnetic field. Thus, an oscillating magnetic field can either be aligned along the z-axis of the flow meter or perpendicular to both z-axis and the static magnetic field. In addition, it is preferred although not required that the first RF magnetic field be substantially uniform in the second volume during some of the pulse sequences used to generate the images of holdup and flow.

Figure 3:
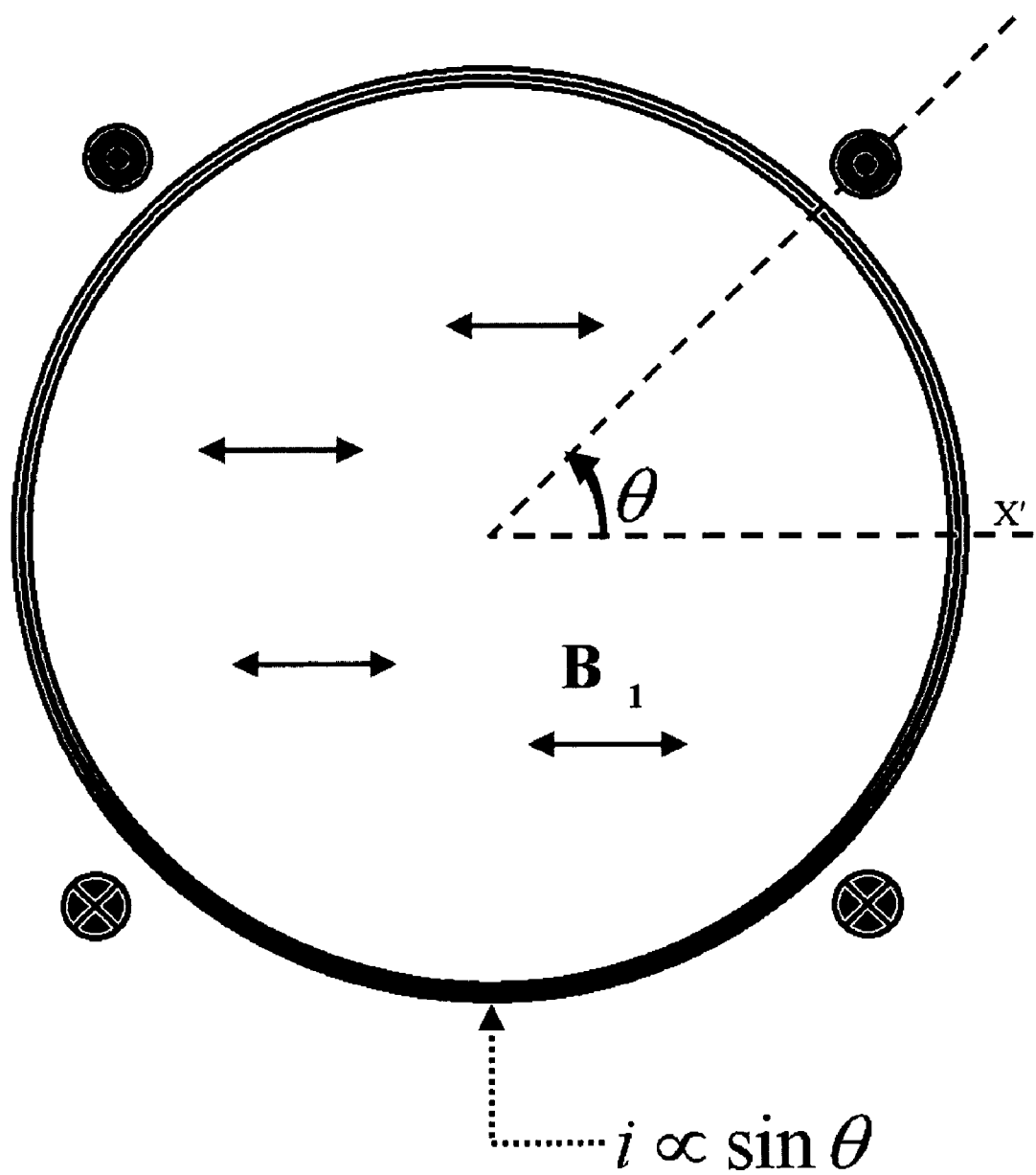
FIG. 3 illustrates a current distribution on a cylinder producing a uniform magnetic field in the interior of the cylinder.

Any method that produces a uniform oscillating magnetic field perpendicular to the cylinder axis of the tool can be used, as is well known by those skilled in the art. However, one method for providing the first oscillating magnetic field B, perpendicular to the cylinder axis of an embodiment of the invention is to generate on the surface of the cylinder a current distribution such that the surface current obeys the following relationship:

$$i \propto \sin \theta, \quad (2)$$

where θ is the azimuthal angle of the cylinder from a local axis of the coil labeled X' as illustrated in FIG. 3. This current distribution is ideal because the field it produces is exactly uniform. However, because it is continuously variable around the cylinder, it can only be approximated. One method of approximation places wires carrying equal currents at specific locations about the cylinder. These locations are given by the following expression.

$$\langle \theta_n \rangle = \frac{1}{2}(\theta_n + \theta_{n-1}), \quad (3)$$

where $$\cos \theta_n = 1 - \frac{2n}{N}, \quad n \in \{0, N\}. \quad (4)$$

N is the total number of turns in the coil. This coil can be used to generate the first oscillating magnetic field when its x'-axis is oriented parallel to the y-axis of the embodiment of the magnetic structure of FIG. 1b. If its x'-axis is oriented parallel to the x-axis in this way it can be used as a shim coil to keep the magnetic field constant as the temperature of the permanent magnets varies while in the well provided the current in the coil produces a magnetic field that varies slowly with time rather than an oscillating current.

Figure 4:
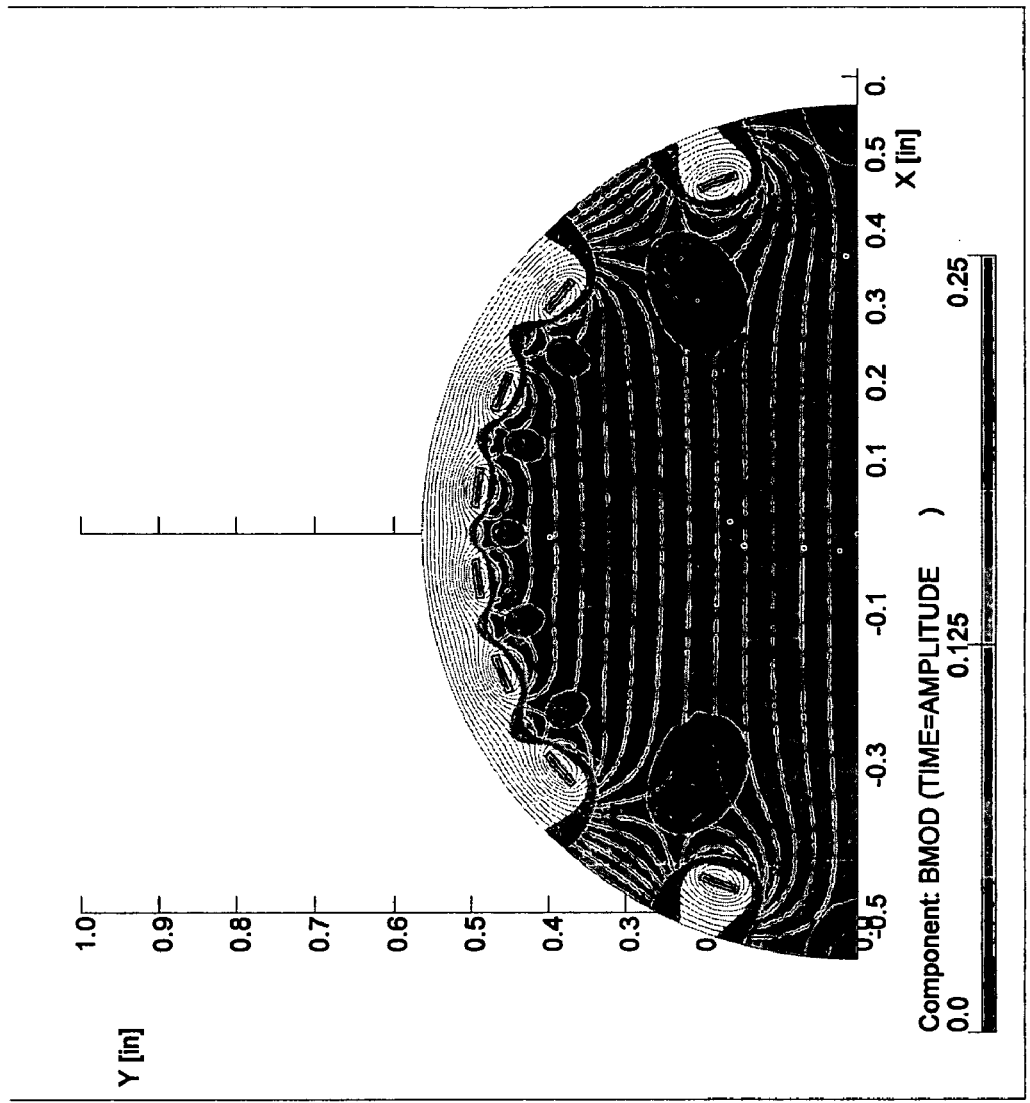
FIG. 4 is a radio frequency (RF) magnetic field for the fixed current approximation to a sin(θ) current distribution.

FIG. 4 illustrates an eight turn fixed current approximation to the current distribution shown in eqn. (2) at a frequency of 5 MHz. Only ½ of the coil is shown because of symmetry. In one example of use, the turns are connected in parallel and the total current is one amp. The coil is inside a conductive housing similar to one that might be present in the construction of the flow meter. The contour shading represents the amplitude of the RF magnetic field parallel to the x-axis. This component of the RF field rotates the magnetization. The component perpendicular to the x-axis will not. The homogeneity of the RF field is satisfactory for the purposes of NMR in the illustrated configuration. The turns of the coil can be connected is series or in parallel to pick the coil inductance, and the number of turns in the coil can be varied to change the RF field homogeneity and coil inductance.

The Means for Generating the Second Oscillating Magnetic Field

Figure 5:
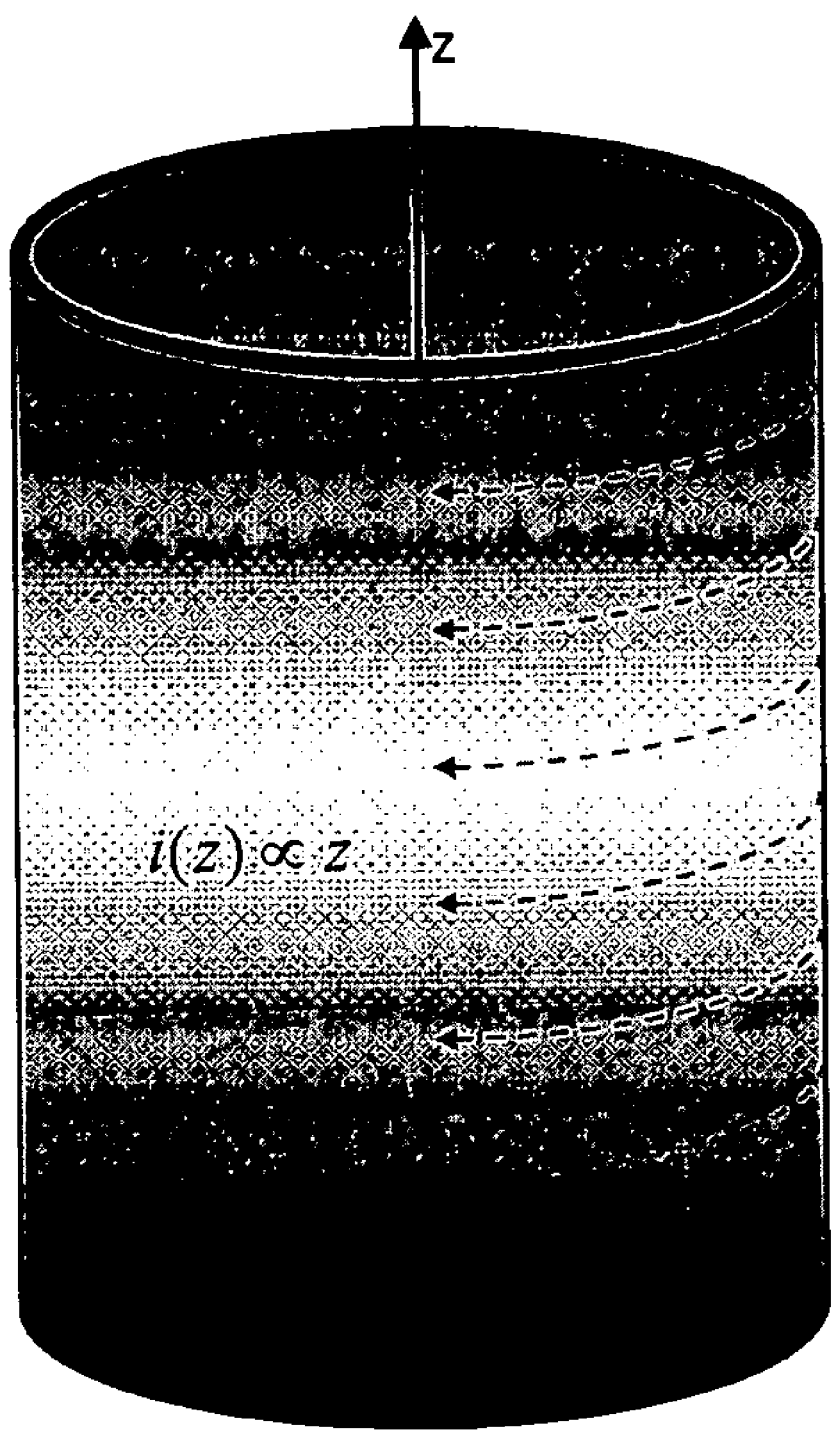
FIG. 5 is a diagram of a current distribution on a cylindrical surface.
Figure 6:
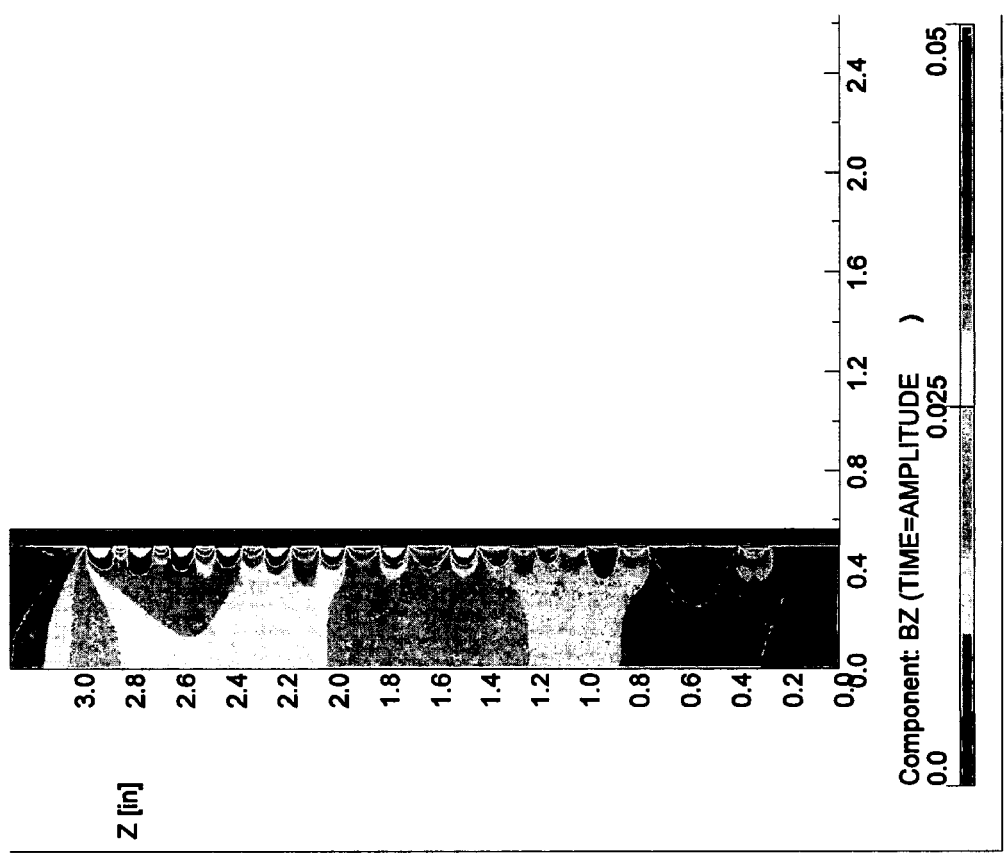
FIG. 6 shows an illustration of an example of Maxwell coil pairs distributed on a cylindrical axis.

To obtain an oscillating magnetic field, g, that varies linearly along the z-axis of a series of Maxwell coils can be used that are arranged on a cylindrical surface oriented parallel to the z-axis. Using the target field method, it can be demonstrated that the continuous current distribution required to produce a linearly varying azimuthal magnetic field within the cylinder is a current sheet flowing azimuthally on the cylinder as shown in FIG. 5. This solution can be approximated by discrete wires where the location of the wires is given by $$\langle z_n \rangle = \frac{L}{2\sqrt{N}}(\sqrt{n} - \sqrt{n-1}), \quad n \in \{1, N\}, \quad (5)$$

where L is the length of the coil and N is the number of Maxwell pairs. The amplitude of $g_z$ generated by these coils is shown in FIG. 6 Those skilled in the art will understand that any other means of generating $g_z$ than described here may be used as well.

Methods

The NMR methods used for this flow meter use relaxation contrast to distinguish between flowing fluid fractions. This procedure is typically referred to as a holdup measurement. To measure flow velocity, rotating-frame imaging methods are used. A general discussion of rotating-frame imaging is given by Hoult. (Hoult, D. I. "*Rotating Frame Zeugmatography*", J. Magn. Reson, (1979) 33, 183-197.) One of the many advantages of using rotating frame imaging methods and relaxation contrasts is that many different types of fluid can be analyzed. For example, the flow can be turbulent or laminar, can be stratified or not. Further, the fluid under analysis can be multiple constituents that have similar physical and molecular properties and yet the constituents can be contrasted. Moreover, there is no need for coils to produce static field gradients for spatial imaging. Accordingly the hardware used is simplified over that of other contrast devices. Another advantage is that transverse relaxation can be measured rapidly that minimizes the issue of changes in the content of the instrument's sensitive volume during measurement. It is to be understood throughout the disclosure of the NMR method used in this invention that appropriate phase cycling techniques are to be used when necessary to select the appropriate signal component and to minimize the effect of undesired signals detected by the system.

Holdup

Figure 7:
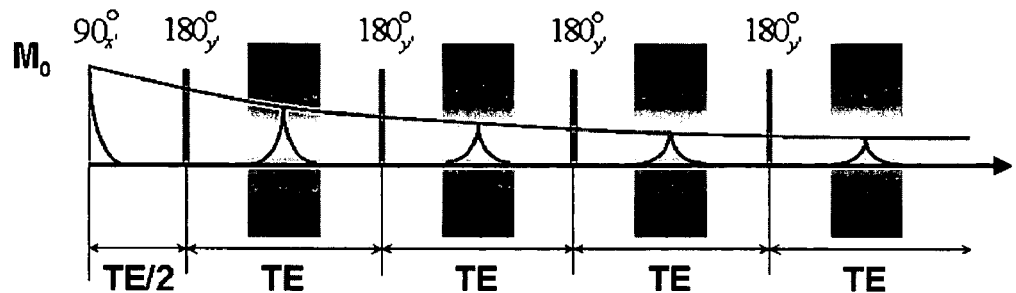
FIG. 7 is an example of a Carr-Purcell_Meiboom-Gill (CPMG) sequence.

Holdup measurements commonly refer to the determination of flowing fractions of crude oil, water, and gas in the well bore. There are several NMR methods that are applicable for determining the fluid fractions in the well bore. The method disclosed herein is relaxation contrast. When relaxation times for crude oil and water are sufficiently different, a Carr-Purcell-Meiboom (CPMG) pulse sequence (shown in FIG. 7) can be used to quantify separately the oil and water NMR signals. Optionally however, signals other than a CPMG sequence can be used here for finding relaxation times. One example of another signal comprises amplitudes from a generalized CPMG sequence where the flip angles are not the nominal 90 and 180 degree angles. This is done by measuring the complex, phase-sensitive amplitude of the spin echoes acquired during the pulse sequence and estimating the magnitude of each echo. These data are transformed into the signal amplitude as a function of relaxation time using the well-known techniques for approximating Laplace transforms. The process is shown below to introduce the nomenclature.

$$\{(e_{x,n}, e_{y,n}), nTE\} \xrightarrow[\text{estimate magnitude}]{} \{e_n, nTE\} \xrightarrow[\text{Transform to } T_2 \text{ space}]{} \{a_n, T_{2n}\}. \quad (6)$$

TE is the echo spacing of the CPMG sequence; $e_{i,n}$ are the phase sensitive echo amplitudes where i is x or y; $e_n$ represents the magnitude of the echoes; $a_n$ represents the amplitudes of the signal in $T_2$ domain; and $T_{2i}$ are the associated relaxation times. This final function is commonly known as a relaxation time distribution. The distribution is integrated up to an empirically determined cut-off value, $T_{2c}$, to estimate the oil signal and the remaining signal is the water signal.

$$A_O = \sum_{T_{2i} < T_{2c}} a_i \quad (7)$$

$$A_W = \sum_{T_{2i} > T_{2c}} a_i$$

Figure 8:
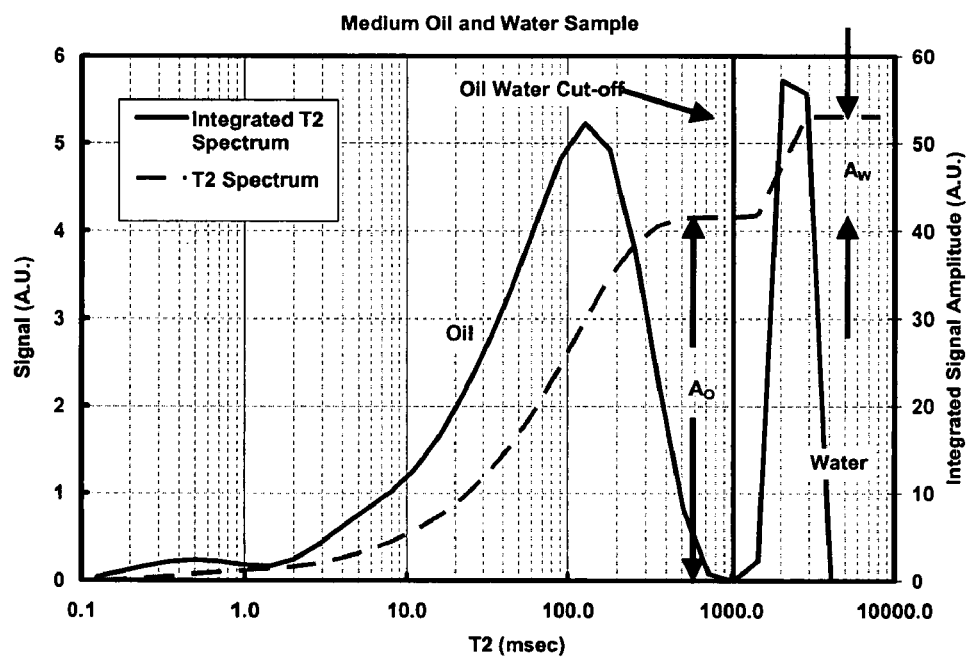
FIG. 8 illustrates a $T_2$ demonstration of a medium weight oil and water sample.

A typical medium oil and water $T_2$ distribution is shown in FIG. 8. The signal is integrated from 0.1 msec to 1000 msec to obtain the oil signal estimate and from 1000 msec to 10000 msec to estimate the water signal. The separation of the signal is insensitive to the value of the cut-off time. In this example, cut-off values in the range from 700 to 1200 msec result in substantially the same oil and water signal amplitude.

Figure 9:
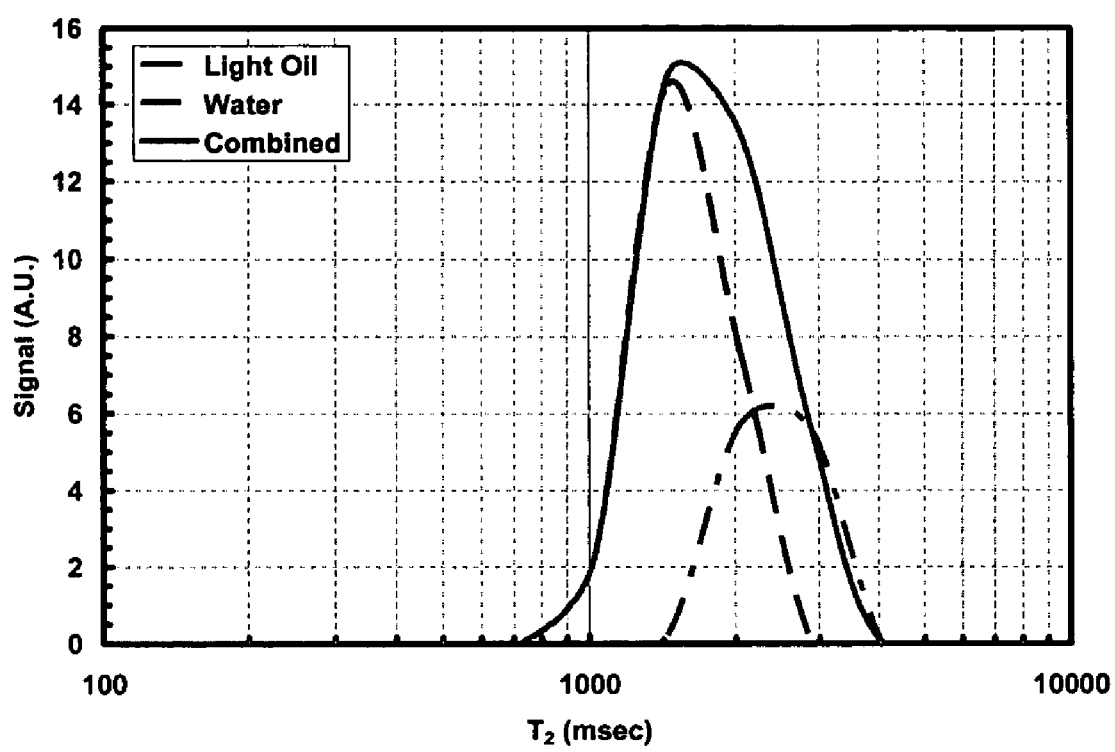
FIG. 9 illustrates a $T_2$ demonstration of a light weight oil and water sample.

However, an example where this technique will fail is illustrated in FIG. 9. In this example, the oil is very light and its relaxation time is substantially the same as the water relaxation time. No cut-off value exists that would sufficiently separate the oil and the water signals. Paramagnetic impurities might reduce the water relaxation time so that it overlaps with even a medium weight oil.

Additional advantages with the method described herein are that this method requires no RF or static magnetic field gradients to estimate holdup. Also, no assumptions are made concerning the flow regime in the instrument. For example, the flow could be slug flow, stratified flow, or bubble flow. It could be turbulent or laminar as well. The only condition that needs to be satisfied for operation of the present method and apparatus is that the fluid be fully polarized. In fact, this condition can be relaxed if calibration experiments are performed to estimate fluid spin-lattice relaxation times. In addition, the $T_2$ spectrum and the fluid flow velocity could be used to estimate the polarization of the fluids and provide a correction factor.

Flow Measurements

Figure 10:
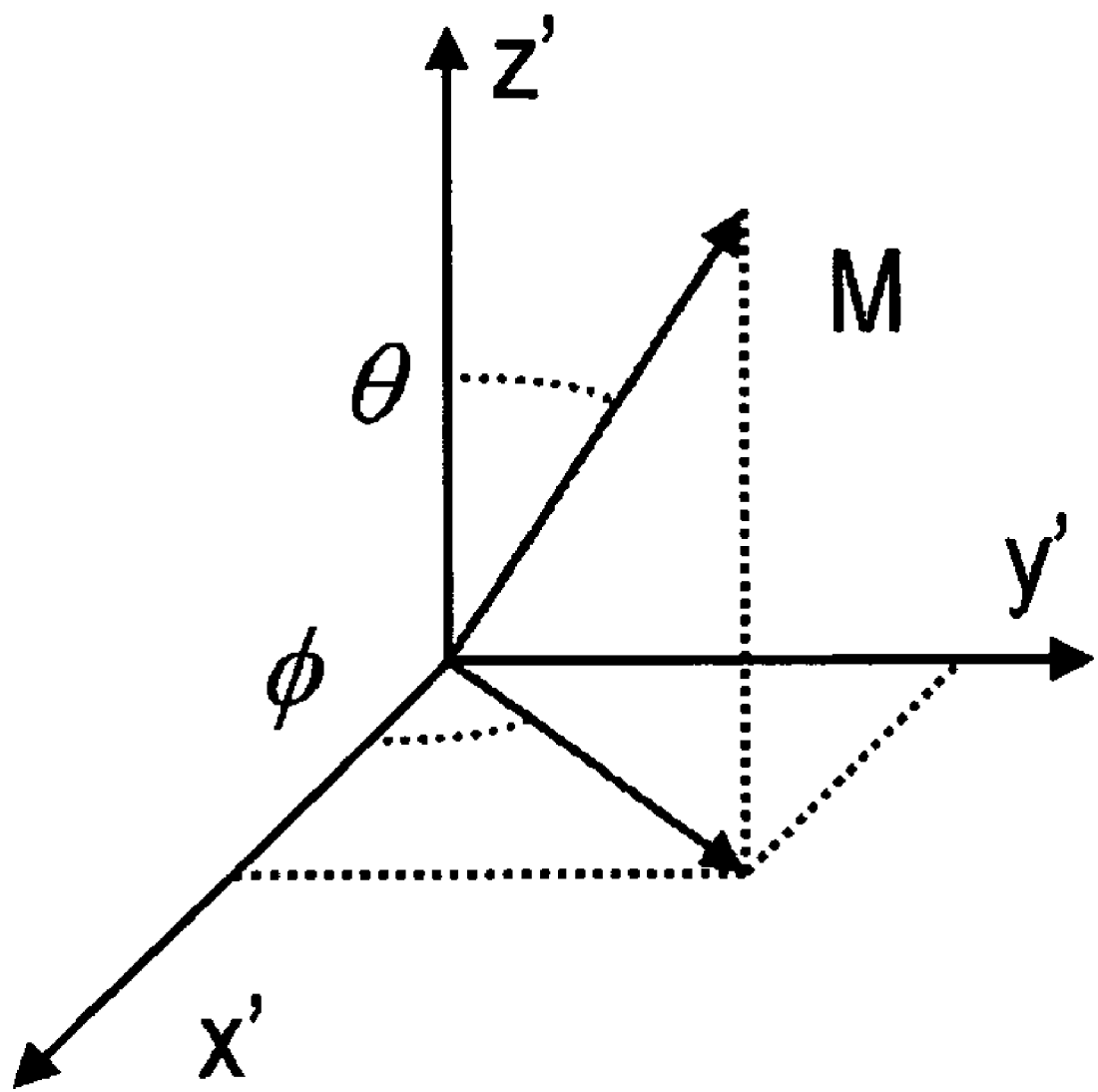
FIG. 10 shows precession and nutation angles.

There is a class of NMR techniques that use spatially dependent RF magnetic fields to produce NMR signals that contain information concerning the displacement or location of individual molecules. This class of techniques is commonly known as rotating-frame zeugmatography.(Hoult). NMR techniques that use static magnetic field gradients to either produce images or measure molecular displacements encode the position of molecules in the precession angle. This is the angle that the transverse magnetization makes with the x- or y-axis in the rotating frame when the RF magnetic field is turned off. Rotating-frame zeugmatography techniques encode the position of molecules in the nutation angle. This is the angle that the magnetization makes with z-axis in the rotating frame. An illustration of these angles is shown in FIG. 10. The angle that the magnetization, M, makes with the z'-axis is the nutation angle, $\theta$. When the magnetization is projected into the x'-y' plane. The angle, is the precession angle.

Many of the techniques that use static magnetic field gradients can be translated into techniques using RF magnetic field gradients simply by replacing the precession angle with the nutation angle in the mathematical formalism and replacing static field gradient pulses with RF field gradient pulses. Fluid flow measurements require at least two gradient pulses. The first encodes the position of the molecules initially. The second decodes the position at a later time. The residual nutation angle is then proportional to the fluid velocity if the field gradient is constant across the sample volume. Those skilled in the art will understand these fluid flow measurements could use more complicated pulse sequences and that the methods disclosed below are illustrative.

Amplitude Modulation

One simple rotating-frame flow measurement technique is (Bourgeois, D. and Decorps, M. "*A $B_1$-Gradient Method for the Detection of Slow Coherent Motion,*" J. Magn. Reson. (1991) 91, 128, 135).

$$g_{z,x} - \Delta - g_{z,-x} - \text{Acquire}. \quad (8)$$

Figure 11:
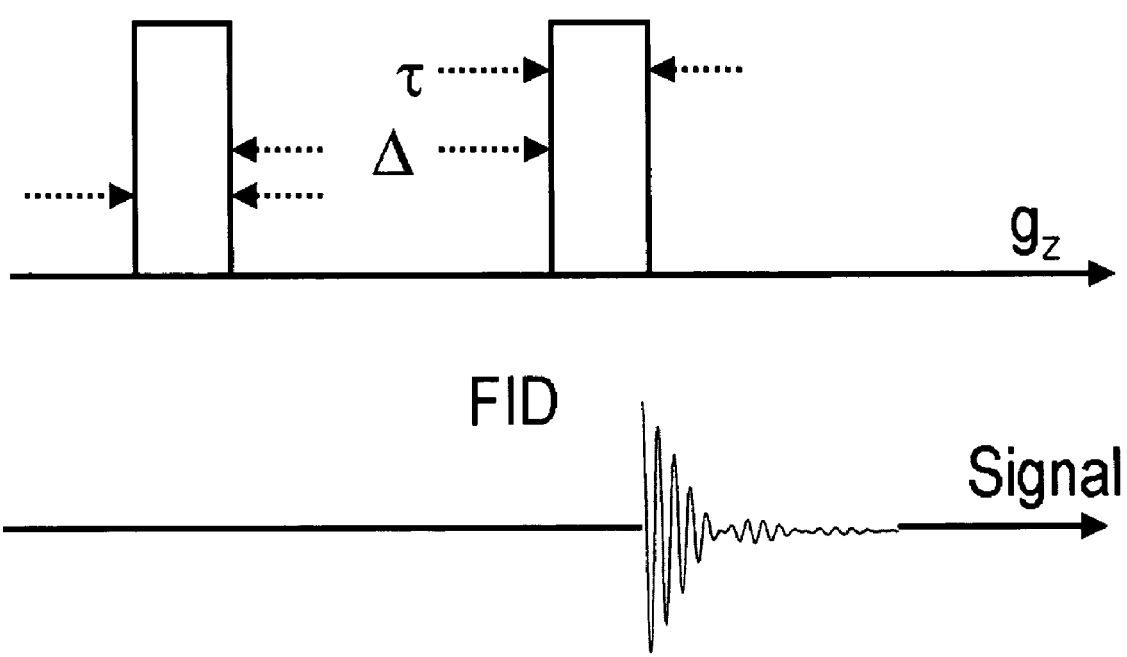
FIG. 11 demonstrates a timing diagram of a simple rotating frame velocity imaging technique.

Here $g_{m,n}$ is the RF field gradient pulse of length, $\tau$, and $\Delta$ is the time between the two gradient pulses. The subscript m represents the orientation of the gradient in real space, and the subscript n is the phase of the pulses or equally, the orientation of the RF field in the rotating frame. A timing diagram illustrating this method is shown in FIG. 11. When relaxation effects are minimal, this pulse sequence produces a free induction decay (FID) that is proportional to the sine of the accumulated nutation angle, $\theta$.

$$f = \frac{1}{2} \int d^3 r M_0(r) \sin(\theta(r) - \theta(r')). \quad (9)$$

Here the nutation angle is given by $$\theta(r) = \gamma g_z z \tau, \quad (10)$$

where $g_z$ is the amplitude of the RF field gradient, z is the location of the magnetization element, and $\tau$ is the amplitude of the pulse. Thus the amplitude of the FID in terms of the fluid average velocity is $$f = \frac{1}{2} \int d^3 r M_0(r) \sin(\xi), \quad (11)$$

where $$\xi = \gamma g_z v_z \Delta \tau. \quad (12)$$

This is the magnetization weighted average of the sine term in the above equation. If there is a single fluid flowing, $M_0$ is known or can be estimated and the fluid velocity extracted from the amplitude of the FID. If more than one fluid phase is flowing, the fluid fraction within the sensitive volume depends on the flow regime, and therefore the magnetization is not known. Thus, one must combine the pulse sequence in eqn. (8) with a pulse sequence that can provide contrast between the different fluid phases.

The method used with the present method and apparatus is relaxation contrast. A series of refocusing pulses is added to the end of the sequence in eqn. (8), (see FIG. 11):

$$g_{z,x}-\Delta-g_{z,-x}-TE/2-180_y-TE-180_y-TE-180_y-TE \qquad (13)$$

Figure 12:
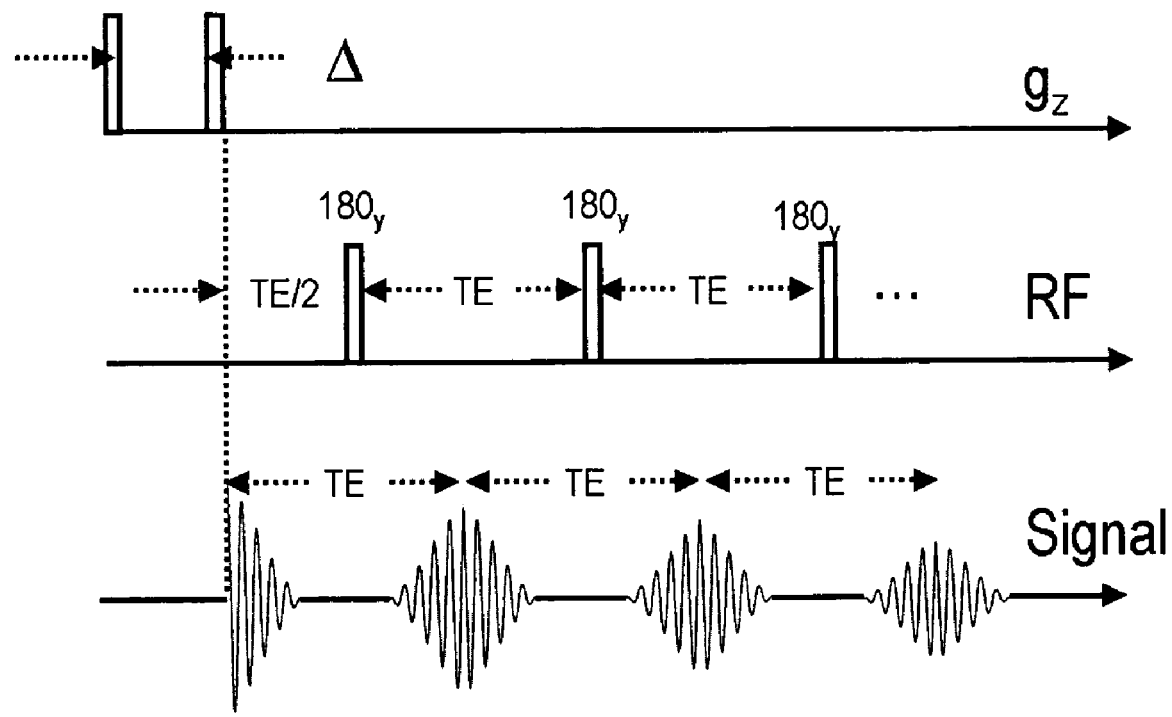
FIG. 12 shows a timing diagram for pulse sequence to simultaneously encode fluid velocity and relaxation into the signal.

Here the echoes produced by the refocusing pulses are acquired. These echoes are transformed into the $T_2$ domain and the resulting spectrum (see for example FIG. 12 and eqn. (6)) is integrated to separate the oil signal from the water signal. This is described in more detail below. The oil and water signals are now known, they are:

$$A_W = \frac{1}{2} V h_W M_{0W} \overline{\sin(\xi_W)} \qquad (14)$$

$$A_O = \frac{1}{2} V h_O M_{0O} \overline{\sin(\xi_O)}$$

In this case the subscripts refer to oil and water for the two flowing phases. A is the amplitude of the integrated signal, V is the volume of the sensitive volume, h is the fraction occupied by the fluid (holdup), and M is the magnetization of the fluid.

In each expression in equation (14) there are two quantities that are unknown. These are the volume fractions of fluids and the velocity dependent sine factor. Thus, the signals need to be calibrated to the fraction of flowing fluid. This is done by using the integrated spectrum from a standard CPMG sequence. The separated signals without the application of the RF gradient pulses are $$A'_W = \frac{1}{2} V f_W M_{0W} \qquad (15)$$

$$A'_O = \frac{1}{2} V f_O M_{0O}$$

The sine factor is estimated by dividing the expressions in eqn. (14) by the corresponding expression in eqn. (15).

$$A_W/A'_W = \overline{\sin(\xi_W)}$$

$$A_O/A'_O = \overline{\sin(\xi_O)} \qquad (16)$$

Figure 13:
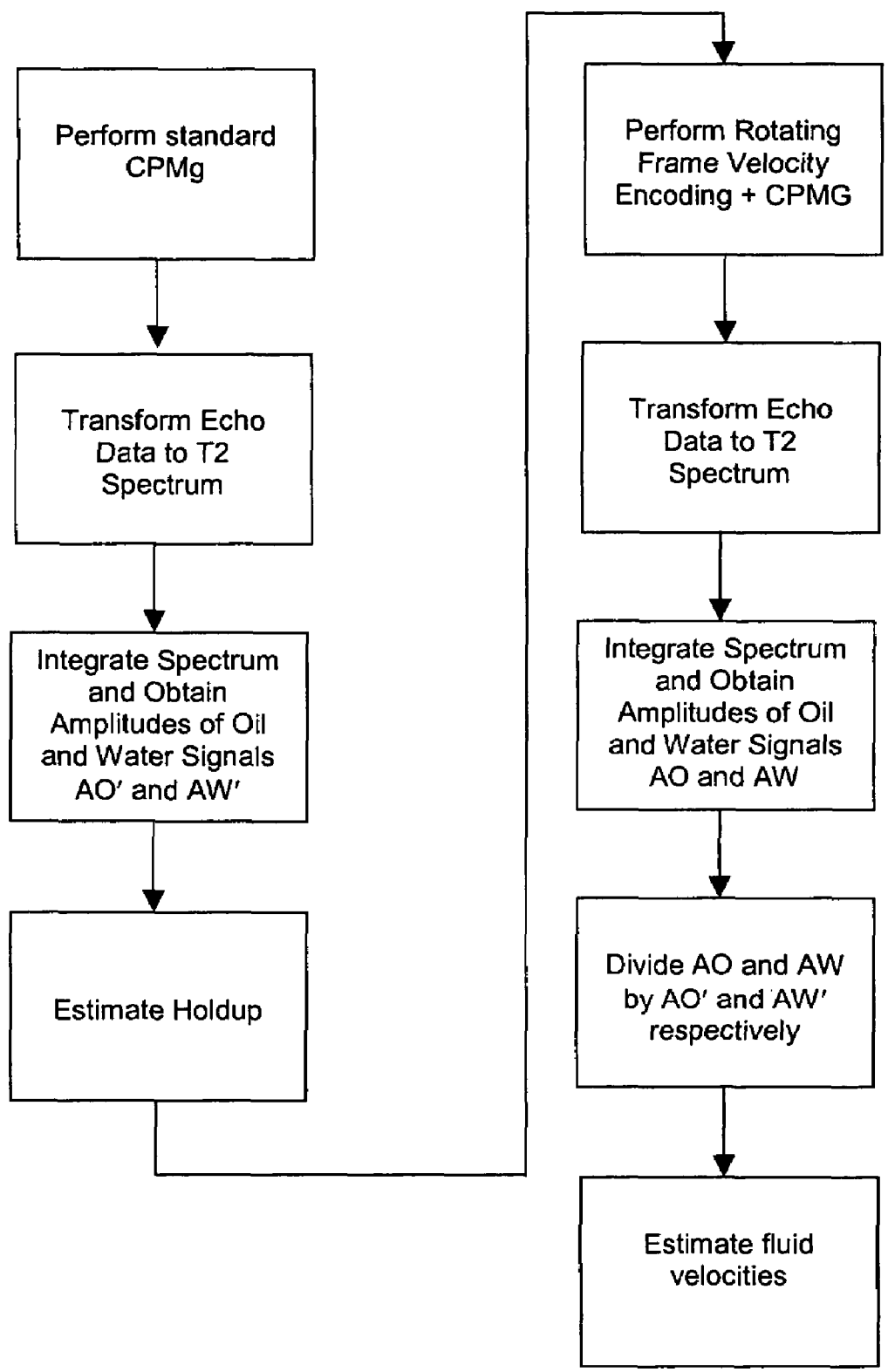
FIG. 13 is an example of a data flow diagram for velocity estimate method.

The velocities are then easily determined. The flow diagram of the process is shown in FIG. 13.

Phase Sensitive Modulation

In addition to generating magnetization along the y-axis, the two RF gradient pulses in eqn. (8) also generate magnetization along the z-axis. The total magnetic moment is given by $$m_y(t = 0_-) = \frac{1}{2} \int d^3 r M_0(r) \sin(\theta(r) - \theta(r')) \qquad (17)$$

$$m_z(t = 0_-) = \frac{1}{2} \int d^3 r M_0(r) \cos(\theta(r) - \theta(r'))$$

If a 90° pulse along the y-axis of the rotating frame is applied immediately after the second RF gradient pulse, then the magnetization is given by $$m_z(t = 0_+) = \frac{1}{2} \int d^3 r M_0(r) \cos(\theta(r) - \theta(r')) \qquad (18)$$

$$m_y(t = 0_+) = \frac{1}{2} \int d^3 r M_0(r) \sin(\theta(r) - \theta(r'))$$

The integrated FID is therefore $$f(0_+) = \frac{1}{2} \int d^3 r M_0(r) \exp\{i(\theta(r) - \theta(r'))\} \qquad (19)$$

$$= \frac{1}{2} \int d^3 r M_0(r) \exp\{i\xi\}$$

Figure 14:
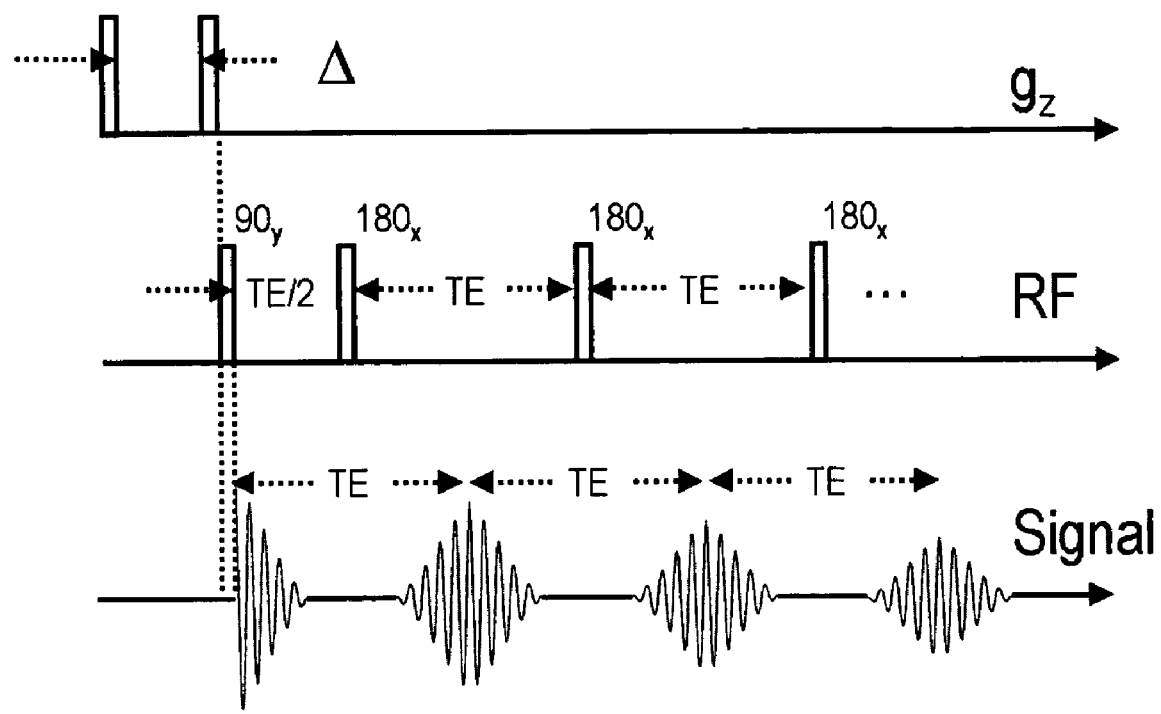
FIG. 14 illustrates a phase encoded velocity measurement pulse sequence.

Thus the velocity is encoded in the phase of the FID. By attaching a series of 180° refocusing pulses to the current sequence, relaxation contrast can be used to separate the oil and water signal from the amplitude of the transverse magnetization. The pulse sequence is shown in FIG. 14, and can be written as $$g_{z,x}-\Delta-g_{z,-x}-90_y-TE/2-180_x-TE-180_x-TE-180_x-TE \qquad (20)$$

Figure 15:
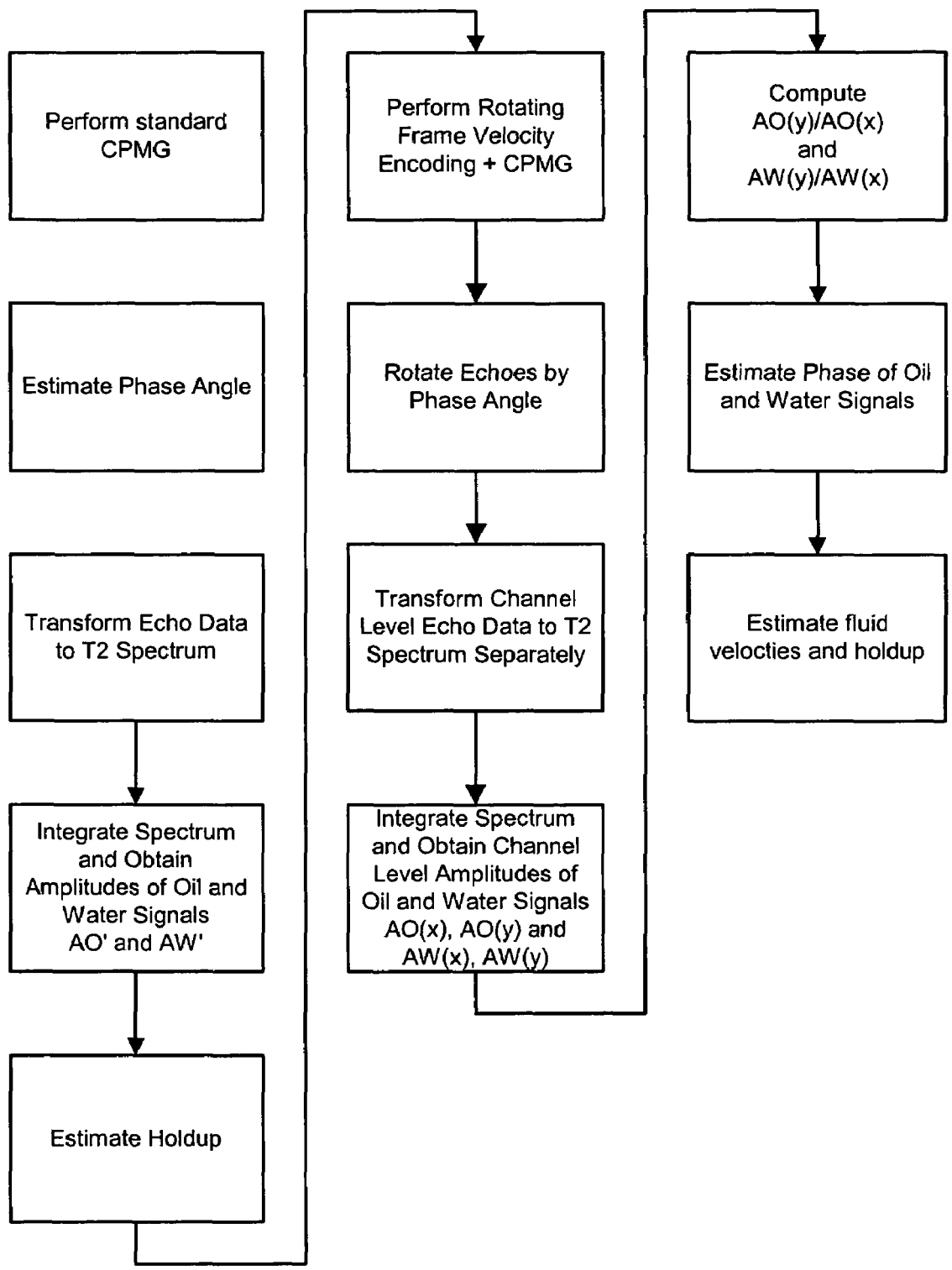
FIG. 15 demonstrates a flow diagram for estimating fluid phase velocities and holdup.

The estimation process of holdup and fluid velocity is more complex using this method than the prior method because the absolute phase of the signal is not known. Usually the signal phase is determined self consistently, and in that case only the velocity difference between fluid phases could be determined. Thus, the absolute phase is a slowly varying function of time and can be determined from a CPMG sequence that is used to estimate holdup. The method is outlined in FIG. 15. First, the complex echo amplitudes from a standard CPMG sequence are acquired at t=nTE.

$$\{e_{x,n}', e_{y,n}'\} = \{e_n' \cos\phi, e_n' \sin\phi\} \qquad (21)$$

where $\phi$ is the phase angle. The phase angle is determined by summing the in-phase and out-of-phase components of the echo $$\tan\phi = \sum_n e'_{y,n} / \sum_n e'_{x,n} \qquad (22)$$

Figure 16:
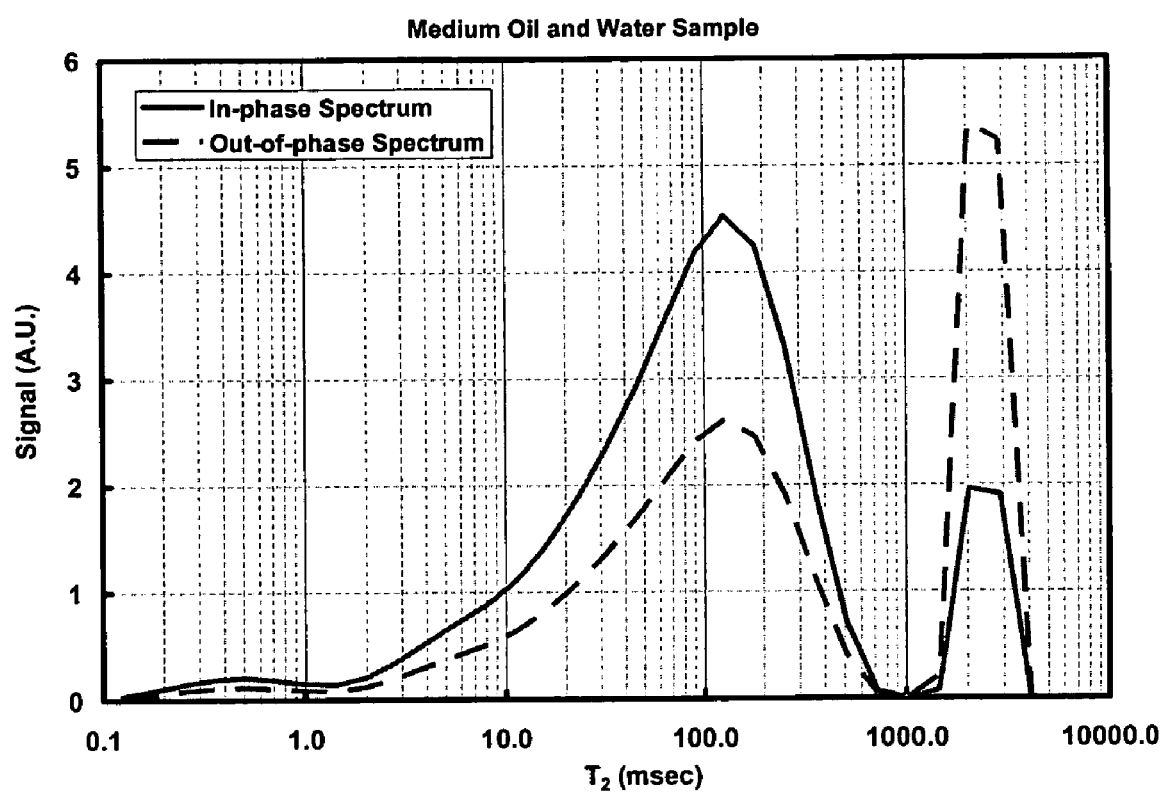
FIG. 16 shows an illustration of in-phase and out-of-phase $T_2$ spectra.

The echoes are rotated by the phase angle and transformed into the $T_2$ domain. The limits of the sum in eqn. (22) are determined by the echo amplitudes to optimize the signal-to-noise ratio of the phase angle. If the SNR is insufficient, a number of standard CPMG sequences acquired at other times can be summed together because $\phi$ is slowly varying. Hold up, h, is determined by the integrated amplitudes of the signal in the $T_2$ domain (see eqn. (15)). Next the echo amplitudes from the phase encoded velocity sequence (eqn. (20) and FIG. 14) are acquired. These are $$e_{x,n} + i e_{y,n} = (e_{O,n} e^{i\xi_O} + e_{W,n} e^{i\xi_W}) e^{i\phi}, \qquad (23)$$

where complex notation has been used. After acquisition each echo is rotated by the angle $-\phi$. The resulting in-phase and out-of-phase components of the echoes are transformed into the $T_2$ domain separately. These yield in-phase and out-of-phase spectra as shown in FIG. 16. In this example the phase of the oil spectrum is 20° and the water spectrum is 60°. The spectra are integrated to obtain the in-phase and out of phase contributions to the oil and water signals $$A_{W,x}+iA_{W,y}=A_W e^{i\overline{\xi_W}}$$

$$A_{O,x}+iA_{O,y}=A_O e^{i\overline{\xi_O}} \quad (24)$$

The fluid velocities are estimated from $$\overline{\tan\xi_j}=A_{j,y}/A_{j,x} \quad (25)$$

and the holdups are estimated from $$A_j=\sqrt{A_{j,x}^2+A_{j,y}^2}. \quad (26)$$

Care must be taken when transforming the echoes to the $T_2$ domain. Because of the velocity dependent phase angle, the commonly used non-negative constraint in the transform must be used with caution. Given some combinations of fluid velocity, RF gradient strength and encoding time, the amplitude of the oil signal, or water signal or both in the $T_2$ domain could be negative. There are several possible remedies. First, estimates of the fluid velocities will exist prior to the use the flow meter. If so, the operator can pick the gradient and encoding time so that the maximum phase angle is 90°. Second, different constraints on the negativity could be applied below and above the $T_2$ cutoff between the oil and water during the transform. Additionally, the inversion process could be modified to estimate an oil phase factor below the $T_2$ cutoff and a different phase factor above the cutoff.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. For example, the permanent magnet could be comprised of a single solid magnet, or a tubular shaped magnet circumscribing the flow tube. Moreover, skilled artisans appreciate that the steps of excitation and refocusing herein described can be accomplished by any manner currently used or later developed. These and other similar modifications will readily suggest themselves to those skilled in the art, and are intended to be encompassed within the spirit of the present invention disclosed herein and the scope of the appended claims.

What is claimed is:

1. A method of measuring fluid flow comprising:
applying a static magnetic field to the flow;
applying at least one electro-magnetic pulse sequence to the flow, said electromagnetic pulse comprising a rotating frame portion and a refocusing portion, wherein the refocusing portion encodes fluid flow molecule position and later in time decodes the fluid flow molecule position and wherein the electro-magnetic pulse sequence produces signals;
measuring the residual nutation angle between the encoded fluid flow molecules and the decoded fluid flow molecules;
estimating fluid velocity using the residual nutation angle between the encoded molecule position and the decoded molecule position; obtaining a fluid velocity value and making the fluid velocity value available to the user for assessing a characteristic of a wellbore.

2. The method of measuring fluid flow of claim 1 wherein the at least one electro-magnetic pulse sequence comprises a CPMG sequence.

3. The method of measuring fluid flow of claim 2 wherein the refocusing pulses in the generalized CPMG are spaced 180° from one another.

4. The method of measuring fluid flow of claim 3 wherein the signals are echoes.

5. The method of measuring fluid flow of claim 2 wherein the rotating frame portion of the electro-magnetic pulse sequence comprises emitting a first magnetic pulse having a gradient in real space substantially aligned with a first axis and having a radio frequency field orientation in the rotating frame that is substantially orthogonal to the first axis and emitting a second magnetic pulse having a gradient in real space substantially aligned with the first axis and having a radio frequency field orientation in the rotating frame that is substantially orthogonal to the first axis in a direction opposite to the radio frequency field of the first magnetic pulse.

6. The method of measuring fluid flow of claim 2 further comprising determining fluid flow velocity from the residual nutation angle between the encoded fluid flow molecules and the decoded fluid flow molecules.

7. The method of measuring fluid flow of claim 6, wherein the fluid holdup is determined by the integrating the amplitudes of the signal echo in the $T_2$ domain.

8. The method of measuring fluid flow of claim 1 wherein the rotating frame portion of the electro-magnetic pulse sequence comprises encoding the position of fluid flow molecules then decoding the position of the fluid flow molecules at a later time.

9. The method of measuring fluid flow of claim 1 wherein the refocusing portion of the electro-magnetic pulse sequence comprises a CPMG sequence.

10. The method of measuring fluid flow of claim 1, wherein the CPMG sequence occurs within an x-y coordinate system and comprises a pulse having an orientation and pattern of $90_y$, $-TE/2-180_x-TE-180_xTE-180_x-TE$ . . . .

11. The method of measuring fluid flow of claim 1 further comprising analyzing the signal echoes to determine fluid holdup.

12. The method of measuring fluid flow of claim 1, wherein the fluid is selected from the list consisting of single phase fluid, two-phase fluid, and three-phase fluid.

13. The method of measuring fluid flow of claim 1, further comprising measuring fluid flow within a wellbore.

14. The method of measuring fluid flow of claim 1, further comprising analyzing the signals to determine characteristics of the fluid.

* * * * *